(12) United States Patent
Koves

(10) Patent No.: US 6,875,900 B2
(45) Date of Patent: Apr. 5, 2005

(54) UPFLOW OLIGOMERIZATION REACTION PROCESS

(75) Inventor: William J. Koves, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 46 days.

(21) Appl. No.: 10/135,958

(22) Filed: Apr. 30, 2002

(65) Prior Publication Data

US 2002/0128531 A1 Sep. 12, 2002

Related U.S. Application Data

(63) Continuation-in-part of application No. 09/689,526, filed on Oct. 12, 2000, now Pat. No. 6,399,843.

(51) Int. Cl.[7] .............................. C07C 2/08; C07C 2/14
(52) U.S. Cl. ........................ 585/510; 585/514; 585/515; 585/520; 585/526; 585/527; 585/529
(58) Field of Search ................................. 585/510, 514, 585/515, 520, 526, 527, 529

(56) References Cited

U.S. PATENT DOCUMENTS

| 4,313,016 A | 1/1982 | Manning ..................... 585/832 |
| 5,877,372 A | 3/1999 | Evans et al. ................ 585/510 |
| 5,895,830 A | 4/1999 | Stine et al. ................. 585/259 |

FOREIGN PATENT DOCUMENTS

EP        0 994 088 A1       4/2000

*Primary Examiner*—Thuan D Dang
(74) *Attorney, Agent, or Firm*—John G. Tolomei; James C. Paschall

(57) ABSTRACT

An oligomerization process for the production of higher aliphatic olefins is disclosed. In the process, a liquid oligomerization feed stream comprising lighter aliphatic olefins is passed to a reactor vessel. The liquid oligomerization feed stream is transported upwardly in the reactor vessel against gravity through a fixed bed of solid oligomerization catalyst under oligomerization conditions. The catalyst has a Hammett acidity value of −4 or less. A liquid oligomerization effluent stream is recovered comprising product higher aliphatic olefins.

19 Claims, 9 Drawing Sheets

Axisymmetric Simulation Configuration of Downflow Reactor with Constant Heat Release Axisymmetric Simulation Configuration of Upflow Reactor with Constant Heat Release Axial Velocity Radial Profile for Constant Heat Release
axial location: 0.3 m from catalyst bed outlet Axisymmetric Simulation Configuration of Downflow Reactor with Reaction Kinetics Axisymmetric Simulation Configuration of Upflow Reactor with Reaction Kinetics i-butylene Radial Distribution
axial location: 0.3 m from catalyst bed outlet

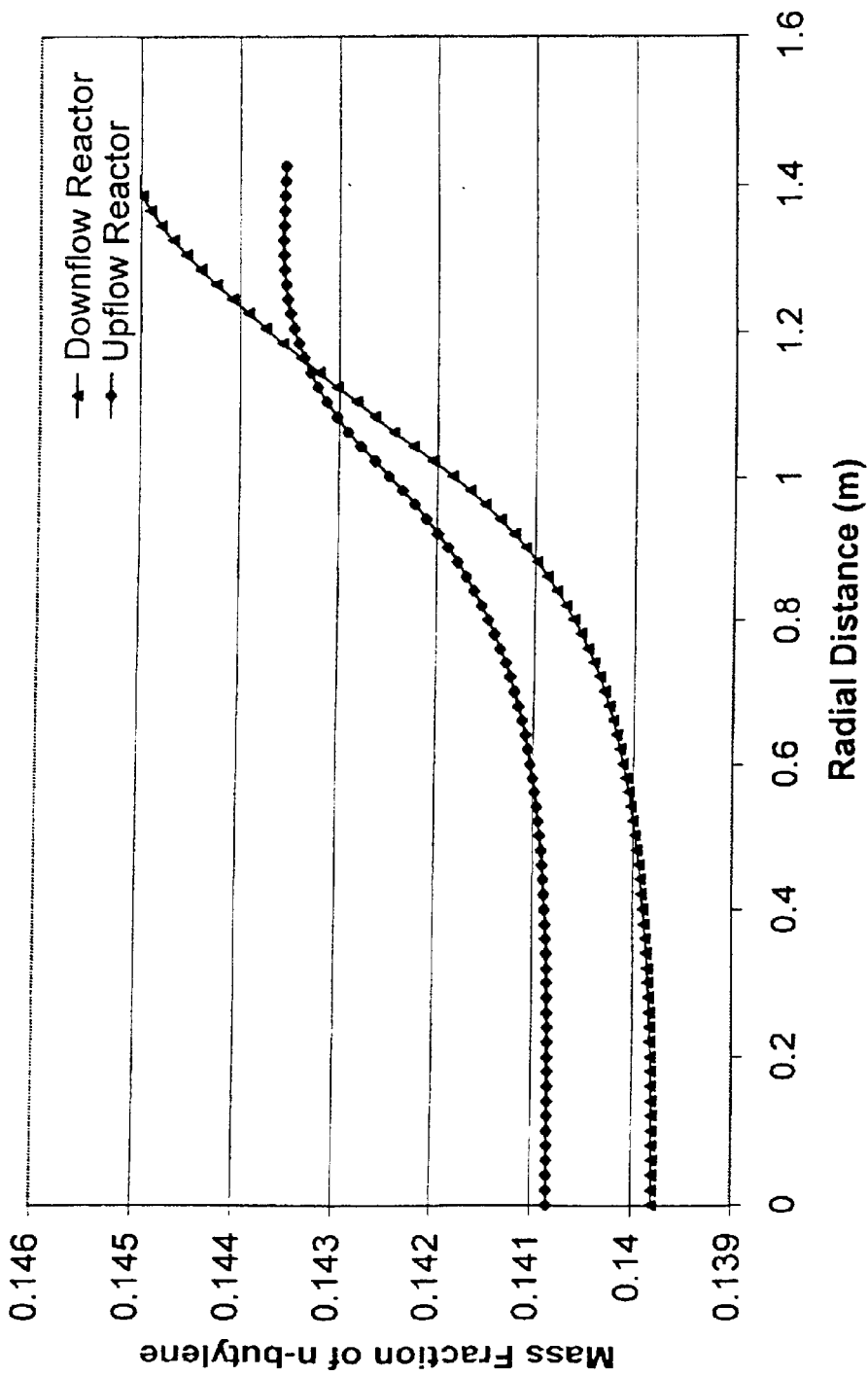

UPFLOW OLIGOMERIZATION REACTION PROCESS

CROSS-REFERENCE TO RELATED APPLICATION

This application is a Continuation-In-Part of application Ser. No. 09/689,526 filed Oct. 12, 2000, now U.S. Pat. No. 6,399,843 the contents of which are hereby incorporated by reference in its entirety.

FIELD OF THE INVENTION

This invention relates generally to the production of higher aliphatic olefins from the oligomerization of lighter aliphatic olefins.

BACKGROUND OF THE INVENTION

Processes for the oligomerization of lighter olefins to produce $C_6$ and higher carbon number olefins are well known. Oligomerization processes can be used to produce plasticizer components from propylene. Additionally, oligomerization processes have been long employed to produce good quality motor fuel from butylene. Such oligomerization processes are also referred to as catalytic condensation and polymerization with the resulting motor fuel often referred to as polymer gasoline. Methods have always been sought to improve the octane number of the gasoline boiling range oligomerization products. In addition, the oligomerization process is also susceptible to catalyst fouling from the condensation of heavy oligomers into coke that covers the catalyst.

Another process that has met the continuing demand for the conversion of light hydrocarbons into high octane motor fuels was the alkylation of isobutane with propylene, butenes and amylenes using a hydrofluoric acid (HF) catalyst, commonly referred to as HF alkylation. The HF process has provided a highly successful method for the production of high octane motor fuels.

A number of arrangements are known for using oligomerization in combination with other processes such as saturation and dehydrogenation as substitutes for acid catalyzed isomerization alkylation. Patents disclosing the dehydrogenation of light paraffin stream with oligomerization of the dehydrogenation effluent include U.S. Pat. Nos. 4,393,259 B1, 5,049,360 B1, 4,749,820 B1, 4,304,948 B1 and 2,526,966 B1.

In the oligomerization method of the indirect alkylation process set forth in, for example, U.S. Pat. No. 5,990,367 B1, lighter aliphatic olefins such as $C_3$ or $C_4$ are contacted with a solid phosphoric acid catalyst in the presence of a higher paraffin diluent such as cyclohexane or octane. The presence of the paraffin diluent is believed to promote the oligomerization in the liquid phase to yield predominantly dimerized butylene or trimerized propylene oligomers such as $C_8$ and $C_9$ olefins. The higher aliphatic olefins can be saturated to provide fuel or plasticizer components.

In an alternative form of the indirect alkylation process, an ionic exchange resin catalyst oligomerizes light olefins to produce oligomers such as $C_8$ olefins. In such processes, the oligomerization zone can be preceded by a dehydrogenation zone to convert paraffinic feed into olefinic feed and/or succeeded by a hydrogenation zone to convert heavy oligomeric olefins into heavy alkanes that can be blended with gasoline stock. U.S. Pat. No. 4,313,016 B1 discloses a heat exchanged oligomerization reactor that contains a cationic exchange resin catalyst. $C_4$ olefins contacted with the resin catalyst oligomerize to $C_4$ oligomers. This patent discloses that water or methanol may be present in small amounts insufficient to form an entrained second phase to serve as a catalyst modifier.

Modern oligomerization processes often include an oxygenate such as tert-butyl alcohol (TBA) and/or sec-butyl alcohol (SBA) in the feed for modifying the catalyst to maintain desired product selectivity. The modifier does not participate in the oligomerization reaction. References disclosing resin catalyzed oligomerization in the presence of an oxygenate modifier include U.S. Pat. No. 5,877,372 B1 and EP 994 088 A1. TBA and SBA have become the resin catalyst modifier of preference.

It is highly desirable to operate the oligomerization reaction under plug flow conditions to assure uniform conversion along the reaction front. Maintenance of plug flow conditions assures a tighter product distribution. Without plug flow conditions, channeling and even recirculation can result. In "channeling", segments of the reaction front move downwardly more quickly than other segments of the reaction front causing bypassing of downstream product fluid by the upstream reactor fluid. This flow instability is also called "fingering" and is a result of the fluid wanting to achieve a lower energy state. "Recirculation" involves swirling of the reactants against the direction of flow. Channeling can cause underconversion and overconversion of reactants to product; whereas, recirculation can have the same effect but to a greater degree. Overconversion can generate even greater temperatures than desired for the oligomerization reaction to proceed and can cause the catalyst to degrade by deposition of carbon particles on the catalyst which is a phenomenon known as "coking". These effects operate to spread the product distribution away from desired products, thereby diminishing product value and consistency. Resin catalyst has a relatively low range of thermal stability. Hence, overconversion can generate reaction temperatures that exceed the range of thermal stability for resin catalyst and cause destruction of the catalyst.

It was originally thought that a downflow reactor scheme would provide sufficient reaction front stability to operate under plug flow conditions. Pilot plant studies did not alert to the fact that plug flow could not be maintained under downflow oligomerization conditions. Modeling was conducted to study the stability of the reaction front under oligomerization conditions. The study revealed not only that downflow aliphatic oligomerization would be unstable, but that it would be far less stable than anticipated. Surprisingly, the modeling study revealed that downflow was so unstable that channeling and even recirculation of reactants could take place under certain conditions.

The density of the liquid mixture in the aliphatic oligomerization reaction decreases proportionally with the progress of the oligomerization. The relatively high heat of reaction from oligomerization generates very high temperatures causing the reaction products to be less dense and more buoyant relative to the reactants even though the higher aliphatic olefin products are more dense than the lower aliphatic olefin reactants at equivalent conditions. The higher temperature effects a greater reduction in density than the composition change increases the density of the products. The viscosity of the liquid mixture in the oligomerization also decreases proportionally with progress of the oligomerization, but the effect of viscosity on stability is much less prominent than is the effect of density. Flow instability occurs when the denser inlet fluid bypasses the less dense product fluid during operation in downflow.

Upflow reactors with and without fixed catalyst beds are disclosed in the art. U.S. Pat. No. 5,789,640 B1 discloses an upflow fluidized bed system using solid acid catalysts. U.S. Pat. No. 4,255,352 B1 discloses upflow through a series of tank reactors to react an olefinic hydrocarbon and an olefinically unsaturated nitrile in the presence of a diluent predominantly comprising water to produce unsaturated dinitriles. The latter patent discloses the use of promoters which it defines to include catalysts without discussion of fixing the catalyst bed. U.S. Pat. No. 6,013,845 B1 discloses producing bisphenol from dimethyl ketone and phenol in a fluidized catalyst bed. Backmixing of catalyst and the reactor feed is minimized by packing the bed with randomly oriented packing.

Both U.S. Pat. Nos. 3,560,167 B1 and 4,801,432 B1 disclose upflow reactors with fixed catalyst beds. Both reactors are equipped for at least one gaseous reactant, although the reactions take place partially in the liquid phase, and mechanical hold-down structures are required to maintain the stability of the catalyst bed.

U.S. Pat. Nos. 4,695,665 B1, 4,051,191 B1 and 4,343,957 B1 disclose upflow processes for the production of cumene using solid phosphoric acid in fixed catalyst beds. The advisability of using an upflow scheme for an oligomerization reaction of aliphatic olefins to obtain plug flow conditions is not disclosed, nor is there any indication of the extent of the instability of an aliphatic oligomerization reaction proceeding in downflow mode.

It is an object of this invention to improve the plug flow stability and product distribution of an aliphatic olefin oligomerization reaction by operating the reaction in an upflow mode.

BRIEF SUMMARY OF THE INVENTION

It has been surprisingly found that operating an oligomerization of lighter aliphatic olefins in the presence of a solid acidic catalyst in an upflow mode enables maintenance of plug flow conditions far better than operation of the oligomerization in the downflow mode. It was not even understood until modeling experimentation was undertaken how poorly the oligomerization of lighter aliphatic olefins would proceed in downflow mode.

Accordingly, an embodiment of the present invention comprises an oligomerization process for the production of higher aliphatic olefins. The process comprises passing a liquid oligomerization feed stream comprising lighter aliphatic olefins to a reactor vessel. The liquid oligomerization feed stream is transported upwardly in the reactor vessel against gravity through a fixed bed of solid oligomerization catalyst under oligomerization conditions. The catalyst has a Hammett acidity value of $-4$ or less. A liquid stream of modifier is passed into contact with the feed stream and the catalyst. Then a liquid oligomerization effluent stream comprising paraffins and product higher aliphatic olefins is then recovered.

In another embodiment of the process of the present invention, the feed stream comprises $C_3$ or higher aliphatic olefins, the catalyst is an acidic catalyst, a liquid stream passed into contact with the feed and the catalyst comprises compounds with at least three carbons and the liquid oligomerization effluent stream comprises $C_6$ or higher olefin product.

A further embodiment of the present invention relates to a process for the oligomerization of lighter aliphatic olefins to higher aliphatic olefins. The process comprises passing a liquid oligomerization feed stream comprising lighter aliphatic olefins and having a first density to a reactor vessel. The liquid oligomerization feed stream is transported upwardly in the reactor vessel against gravity through a fixed bed of solid oligomerization catalyst under oligomerization conditions. The catalyst has a Hammett acidity value of $-4$ or less. Lastly, a liquid oligomerization effluent stream comprising product higher aliphatic olefins and having a second density that is less than the first density is then recovered.

Other objects, embodiments and details of this invention will be provided in the following detailed disclosure of the invention.

BRIEF DESCRIPTION OF THE DRAWINGS

FIG. 9 is a plot of normal butylene radial distribution comparing the models represented in FIGS. 6 and 7.

DETAILED DESCRIPTION OF THE INVENTION

Figure 1:
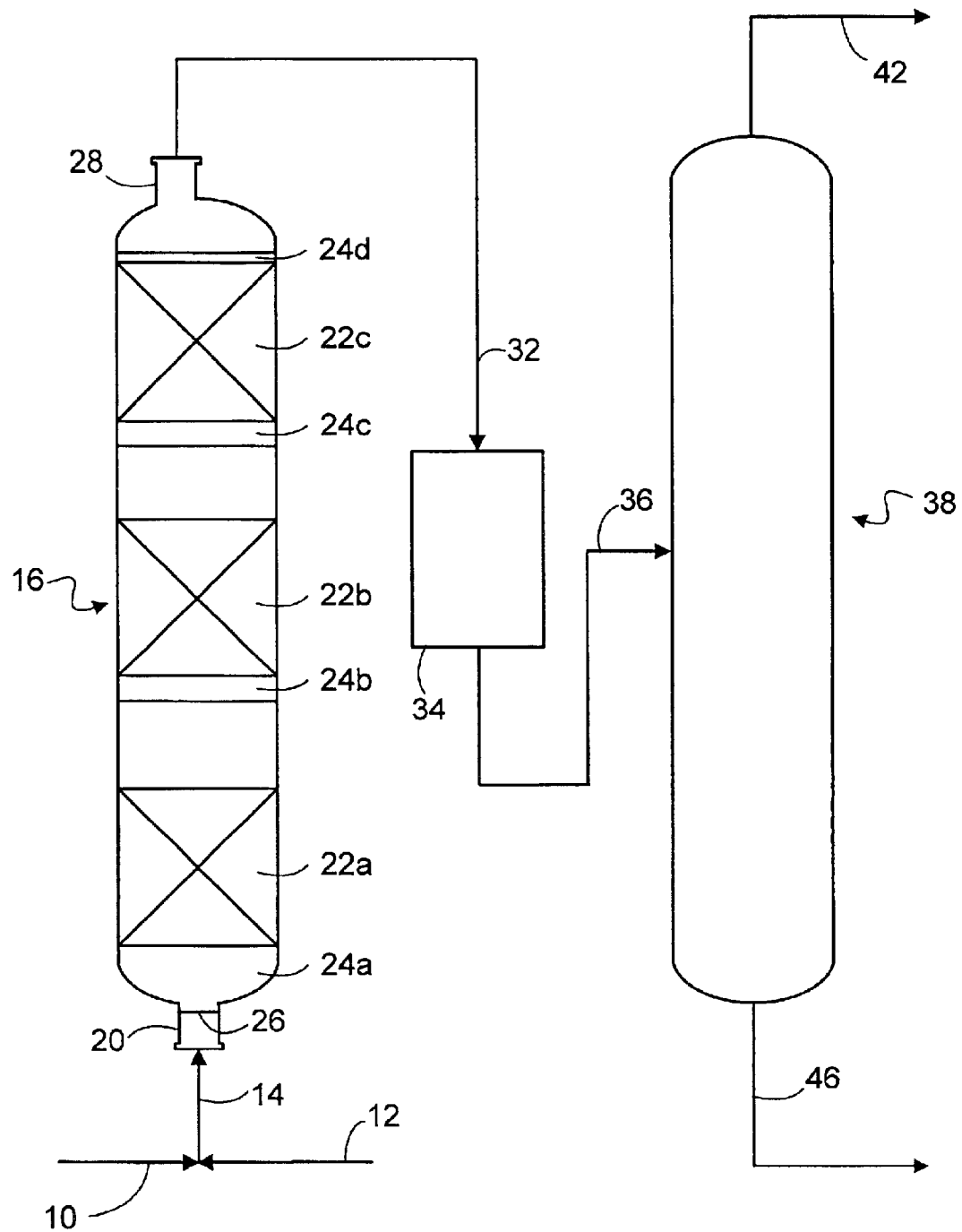
FIG. 1 is a process flow diagram of the present invention.

The essential operational zone for the practice of this invention is the oligomerization reaction zone. Suitable oligomerization zones for this invention take on many forms. The oligomerization process is known by many names such as catalytic condensation and also catalytic polymerization. Known catalysts for effecting such reactions include heterogeneous catalyst such as solid acids and homogenous catalysts, in particular halogenated catalysts such as boron trifluoride as described in U.S. Pat. Nos. 3,906,053 B1, 3,916,019 B1 and 3,981,941 B1.

Preferred catalyst for the oligomerization reaction can generally be described as protonic acids. The preferred acids will generally have a Hammett acidity function of $-4.0$ or less. Examples of catalysts falling into this category include ion exchange resin catalysts, such as sulfonated ion exchange resins, and phosphoric acid catalysts. A particularly preferred catalyst is a solid phosphoric acid ("SPA") catalyst which has a Hammett acidity function of approximately $-5.0$ or lower. The SPA catalyst refers to a solid catalyst that contains as a principal ingredient an acid of phosphorous such as ortho-, pyro- or tetraphosphoric acid, SPA catalyst is normally formed by mixing the acid of phosphorous with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fuller's earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this composition such as a lower phosphoric acid content are however possible. Further details as to the composition and production of SPA catalysts may be obtained from U.S. Pat. Nos. 3,050,472 B1, 3,050, 473 B1 and 3,132,109 B1 and fro other references.

A particularly preferred catalyst is a sulfonic acid ion-exchange resin catalyst. This resin catalyst comprises sulfonic acid groups and can be prepared by polymerizing or copolymerizing aromatic vinyl compounds followed by sulfonating. Examples of aromatic vinyl compounds include the following: styrene, vinyl toluene, vinyl naphthalene, vinyl ethylbenzene, methyl styrene, vinyl chlorobenzene and vinyl xylene. An acidic ion-exchange resin contains typically approximately 1.3 to 2.0 sulfonic acid groups per aromatic group. Preferred resins are those based on copolymers of aromatic monovinyl compounds and aromatic polyvinyl compounds and in particular divinyl compounds in which the concentration of polyvinyl benzene is approximately 1 to 20 wt-% of the copolymer. The particle size of the ion-exchange resin is preferably approximately 0.15 to 1 mm. Furthermore, perfluorosulfonic acid resins consisting of copolymers of sulphonylfluorovinyl ethyl and fluorocarbon compounds can be used. Various suitable ion-exchange resins are commercially available under the name, for example, Amberlyst.

Oligomerization zones in general are maintained at conditions which may vary widely due to the previously listed variables. In this invention, the oligomerization reaction zone is preferably operated at temperatures and pressures that increase the compatibility of its effluent conditions with the inlet conditions of the saturation reaction zone inlet and its inlet conditions with the dehydrogenation reaction zone effluent conditions. When SPA catalyst is used, the preferred temperature of the oligomerization reaction zone may be in a range of from 38° to 260° C. (100° to 500° F.), will typically be in a range of from 93° to 260° C. (200° to 500° F.), and will more typically be in a range of from 149° to 232° C. (300° to 450° F.). When practicing this invention the preferred operating pressure for the SPA catalyst will be in a range of from 690 to 10342 kPa (100 to 1500 psig) and more typically in a range of from 1379 to 6895 kPa (200 to 1000 psig) with pressures of 1379 to 3447 kPa (200 to 500 psig) being particularly preferred. Oligomerization conditions may also include a liquid hourly space velocity (LHSV) of 0.5 to 8 hr$^{-1}$. It has also been found that maintaining operating temperatures in a narrow range of from 149° to 204° C. (300° to 400° F.) can push selectivity toward the production of more $C_8$ isomers when $C_4$ is in the feed.

The temperature of the oligomerization reaction zone in which a resin catalyst is used is typically 0° to 250° C. (32° to 482° F.) and preferably 40° to 150° C. (104° to 302° F.). Pressures in the oligomerization zone using the resin catalyst will be sufficient to maintain the liquid phase, typically 345 to 3447 kPa (50 to 500 psig), and preferably 1380 to 2413 kPa (200 to 350 psig). Oligomerization conditions may also include a liquid hourly space velocity (LHSV) of 0.5 to 20 hr$^{-1}$ with 1 to 6 hr$^{-1}$ being preferred.

The feed to the oligomerization zone reaction will typically comprise $C_3$ to $C_5$ aliphatic olefins, but may comprise olefins have carbon numbers of 12 or higher. Steam or water may be fed into the reactor to maintain a low water content for hydration of the preferred SPA catalyst. A modifier such as TBA or SBA may be added to the reactor if a resin catalyst is used to attenuate the catalyst. The source of the olefin feeds are typically a light gas stream recovered from the gas separation section of an FCC process, $C_4$ streams from steam cracking and coker off gas, $C_3$ streams such as from a separator section of a modified FCC process or the effluent from a dehydrogenation zone. In most operations, this olefin feed stream will contain at least 10 wt-% $C_4$ olefins but it may also constitute all or substantial quantities of $C_3$ olefins. Typically the olefin feeds can have a $C_3$ to $C_5$ olefin concentration of at least 30 wt-%. Where $C_4$ olefins are predominant in the feed, the principal oligomerization products comprise $C_8$ and heavier olefins. Where $C_3$ olefins are predominant in the feed, these olefins will primarily combine to produce $C_9$ and higher olefins. Preferred feeds will have a concentration of at least 30 wt-% and more preferably at least 50 wt-% total olefins in the feed stream. The olefin content of the feed may predominately comprise normal olefins of a single carbon number.

In the practice of this invention using an SPA catalyst, a diluent stream comprising olefin or preferably paraffin components contact the catalyst in conjunction with the usual oligomerization zone feed. The diluent components will preferably comprise heavy hydrocarbons having at least 6 carbon atoms, preferably at least 7 carbon atoms, and more preferably at least 8 carbon atoms. Diluent components having up to 20 carbon atoms may be used. Moreover, diluent components may comprise hydrocarbons having a substantially different carbon number than the product oligomers to facilitate separation of the product oligomers from the diluent. Cycloparaffins are also suitable components for the diluent stream. However, branched $C_8$ paraffins are the preferred diluent component.

The presence of the heavy hydrocarbons promotes liquid phase conditions in the oligomerization zone. The combined heavy diluent stream and feed will usually maintain at least partial liquid phase conditions in the oligomerization zone. Preferably, essentially all, i.e. at least 90 wt-%, of the fluid in the oligomerization zone will be in liquid phase.

The effective washing action of the heavy hydrocarbon diluent requires a minimum liquid mass flux. Preferred rates for the liquid mass flux will exceed 14,648 kg/hr/m$^2$ (3000 lb/hr/ft$^2$). However, if the preferred SPA catalyst is used, the liquid mass flux rate should not be so high that the fluid velocity exceeds 3.07 meters per second (10.07 feet per second) or a mechanical hold down structure would have to be installed in the reactor vessel to prevent the fluid flow from urging the catalyst bed upwardly. For the resin catalyst, oxygenate modifier should comprise 0.2 to 5.0 wt-% of the total feed to the reactor vessel. Alternatively, in the practice of the invention using a resin catalyst, a water-soluble, oxygenate modifier such as an alcohol with at least three carbons and preferably tert-butyl alcohol (TBA) and/or sec-butyl alcohol (SBA) is added to the oligomerization reactor to attenuate the resin catalyst but not to participate in the oligomerization reaction.

The heavy hydrocarbon diluent or oxygenate modifier components may enter the process with or separately from the incoming feed or may be injected into an oligomerization reaction zone at intermediate locations within a single catalyst bed or a number of catalyst beds. It is preferred to have the heavy hydrocarbon diluent or oxygenate modifier present as the feed initially enters the reaction zone to maximize their benefit to the process. In such cases, it is typical to have at least 40 wt-% and more often 50 wt-% or more of the total heavy hydrocarbon diluent stream enter the reactor vessel with the feed. Additional quantities of the heavy hydrocarbon diluent may be injected in stages through the process to maintain temperature control throughout the bed or beds of oligomerization catalyst. It is preferable to have all of the oxygenate modifier enter the first reactor vessel with the feed.

The oligomerization zone preferably has a fixed bed of catalyst that may be in a multiple bed arrangement. The catalyst beds are preferably contained within one or more cylindrical, vertically oriented vessels. The catalyst in multiple beds within the oligomerization zone may be configured in what is known as a chamber-type reactor structure. In a chamber-type reactor vessel, the reactants flow through a series of large diameter catalyst beds. Typically, a chamber-type reactor vessel will contain about five catalyst beds. The temperature of the reactants may be further controlled by recycling to the catalyst beds the relatively inert paraffin saturate stream which acts as a heat sink. Oligomerization reaction zones are routinely arranged with such multiple beds of catalyst that receive an intermediate injection of a quench material to control temperatures from the exothermic reaction. Substantial advantage can be obtained by adding the heavy hydrocarbons as an intermediate injection stream that also benefits the process by serving as a quench stream.

With the addition of the saturated diluent stream, the combined feed to the oligomerization zone will preferably have a ratio of paraffins to olefins of from 1:1 to 5:1. Thus the overall paraffin concentration of the feed to the oligomerization reaction zone will typically be at least 50 wt-% and more typically at least 70 wt-%. The olefin conversion will typically range from 80 to 99 wt-%.

The effluent from the oligomerization reaction zone will normally enter a separator train. The usual separator train for recovery of the product oligomers recovers unreacted feed as an overhead stream. Separation of the effluent stream from the oligomerization zone will also at minimum recover the heavy hydrocarbons from the effluent. Heavy hydrocarbons may be recycled as diluent to the oligomerization zone when SPA catalyst is used either before, but preferably after they are saturated. At least a portion of the modifier stream is also recovered in the separation train for recycle to the oligomerization zone that uses a resin catalyst.

The source of the heavy hydrocarbons for transport to the oligomerization zone can be any stream that can supply the higher carbon number hydrocarbons in the necessary quantities. The paraffinic hydrocarbons can be imported into the process from external sources or produced by saturating all or a portion of the oligomerization effluent stream. (Unless otherwise noted the term "portion" when used herein to describe a process stream refers to either an aliquot portion of the stream or a dissimilar fraction of the stream having a different composition than the total stream from which it was derived.) The entire effluent from the oligomerization zone may be saturated to provide a source of recycle paraffins for the process as well as saturated product oligomers. Alternatively, the effluent may be separated as described to recover the portion of the paraffins that are recycled to the oligomerization zone. If olefinic hydrocarbons are used as a diluent, they may also come from external sources as well or be a recycled portion of the oligomerization effluent stream.

It was found to much surprise that this oligomerization reaction does not provide a stable plug flow condition in downflow mode. Indeed, Computational Fluid Dynamic modeling revealed, despite no indication from pilot plant operation, that channeling can occur during oligomerization in downflow mode, thereby disrupting plug flow conditions. It was also found under certain conditions that the liquid flowing through fixed catalyst beds could even recirculate, that is, begin to flow upwardly in a downflow reactor scheme. These types of non-plug flow conditions can cause both underconversion and overconversion of the reactants which spreads the product distribution and can cause higher reaction temperatures which would operate to degrade or destroy the catalyst. However, it was found that operation of the oligomerization in an upflow scheme maintains plug flow conditions and avoids these surprisingly severe problems.

All other things being equal, an upflow reactor will require no more energy consumption than a downflow reactor of similar design. In a downflow reactor, the reactants must be pumped through a line outside of the reactor to the top of the reactor to the reactor inlet and pumped downwardly through the catalyst beds in the reactor. Whereas, in the upflow reactor, the reactants will have to be pumped from the bottom of the reactor through the catalyst beds to the outlet at the top of the reactor which is at the same relative height as the reactor inlet of the downflow reactor. It is believed that the same pressure will be required to pump fluid to the top of the downflow reactor and down through the downflow reactor as from the bottom of the upflow reactor to the top of the upflow reactor.

The process and different operational steps will be described in conjunction with the process flow diagram in FIG. 1. FIG. 1 shows only limited forms of the invention and only those portions of the process that are necessary to gain an understanding of the invention and the necessary means of integrating the principal processing steps that comprise the invention. Further details related to valves, control means, pumps, compressors, coolers and other necessary processing equipment are well known to those skilled in the art and not described in detail unless necessary for an understanding of the invention.

FIG. 1 shows an oligomerization feed stream, rich in lighter aliphatic olefins brought into the process by a line 10 and combined with a stream carried by a line 12 of recycled heavy paraffins if SPA catalyst is used or TBA or SBA modifier if resin catalyst is used in the process. The line 10 may carry oligomerization feed from a dehydrogenation zone (not shown) but other previously mentioned sources of feed are also suitable. A line 14 carries the combined feed and recycled paraffin or modifier stream into an oligomerization reactor vessel 16 through an inlet nozzle 20 wherein the feed and paraffins contact a catalyst in beds 22a–c. Any type of reactor vessel used to react reactants in the presence of catalyst is generally suitable in practicing this invention. However, cylindrical reactor vessels are preferred for their simplicity. The reactor vessel 16 can comprise tubing, pipes, jets or other common means for introducing reactants into the reaction zone of the reactor vessel 16. It may be preferable to introduce feed and/or saturate at higher levels in the reactor vessel 16, such as at the catalyst beds by interbed distributors (not shown). Additionally, it may also be preferable to bring the saturate stream and the feed stream into the reactor vessel 16 by different lines.

Preferably, the bottom portion of the reactor vessel 16 is filled with an aggregate layer 24a. The amount of such aggregate is not critical to the invention. However, sufficient aggregate should be present to provide support to the reactor vessel 16 internals and disperse the flow of reactants such that plug flow is achieved at the inlet to the catalyst bed. This aggregate layer 24a can comprise any material which will not easily fluidize and is essentially inert to the reactants and products produced in the reactor vessel 16. Preferably, this aggregate layer 24a is comprised of alumina balls. Crushed firebrick and inert ceramic balls are also suitable. The catalyst beds 22a–c are packed above each respective layer of aggregate 24a–c. The plate 26 disposed in the inlet nozzle 20 to support the aggregate layer 24a may be configured to facilitate fluid distribution. The aggregate layer 24d may also be disposed above the top catalyst bed to minimize the potential for catalyst fluidization. A structural hold-down screen (not shown) may also be installed over the top of the aggregate layers 24b–d to further withstand catalyst fluidization. Preferably, about 10 to about 50% volume of the reactor vessel 16 is taken up by catalyst as determined when dry.

A stream 32 carries an oligomerization effluent comprising unreacted lighter olefins, product higher aliphatic olefins and paraffins out an outlet nozzle 28. A stream 32 may carry the oligomerization effluent to a saturator unit 34 to saturate the olefins if SPA catalyst is used or otherwise directly to a separator distillation column 38. If resin catalyst is used in the oligomerization reactor vessel 16 or if no paraffinic recycle is used with the SPA catalyst, it is not necessary that the stream 32 be saturated at this point. If a saturator is used at this point in the process, a feed line 36 carries saturated feed from the saturator unit 34 to the distillation column 38. The distillation column 38 separates lighter hydrocarbons exiting in an overhead stream 42 from heavier hydrocarbons exiting in a bottoms stream 46. Additional separation (not shown) may be necessary to separate TBA or SBA modifier from one or both of the streams 42, 46. Product heavy hydrocarbons may be collected from bottoms stream 46. A portion of the heavier hydrocarbons or modifier may be recycled back to the oligomerization reactor vessel 16 via the line 12 depending on whether the oligomerization reactor vessel 16 uses SPA or resin catalyst, respectively.

To more fully demonstrate the attendant advantages of the upflow oligomerization scheme of the present invention over the downflow scheme, the following modeling results are described.

EXAMPLE 1

A comparison was made of an upflow oligomerization process versus a downflow oligomerization process using Computational Fluid Dynamics modeling. The upflow reactor was assumed to have a diameter of 2.9 meters and a catalyst bed height of 2.5 meters. A constant heat release was assumed along the axial length of a catalyst bed. The density and viscosity of the liquid were made a function solely of temperature. It was assumed that only butylene would be in the feed stream as a reactant with the remainder being paraffin diluent. Inlet conditions included mass fractions of isobutylene at 0.1191, of normal butylene at 0.1889 and paraffin diluent, comprising mostly octanes, at 0.6920. Moreover, the inlet temperature was assumed to be 103° C. and the outlet temperature was assumed to be 126° C. The inlet velocity was assumed to be 1.03 meters per second. The inlet viscosity was calculated to be $1.44 \times 10^{-4}$ kg/m/s and the inlet density was calculated to be 567 kg/m$^3$. The outlet viscosity was calculated to be $1.25 \times 10^{-4}$ kg/m/s and the outlet density was calculated to be 533 kg/m$^3$.

Figure 2:
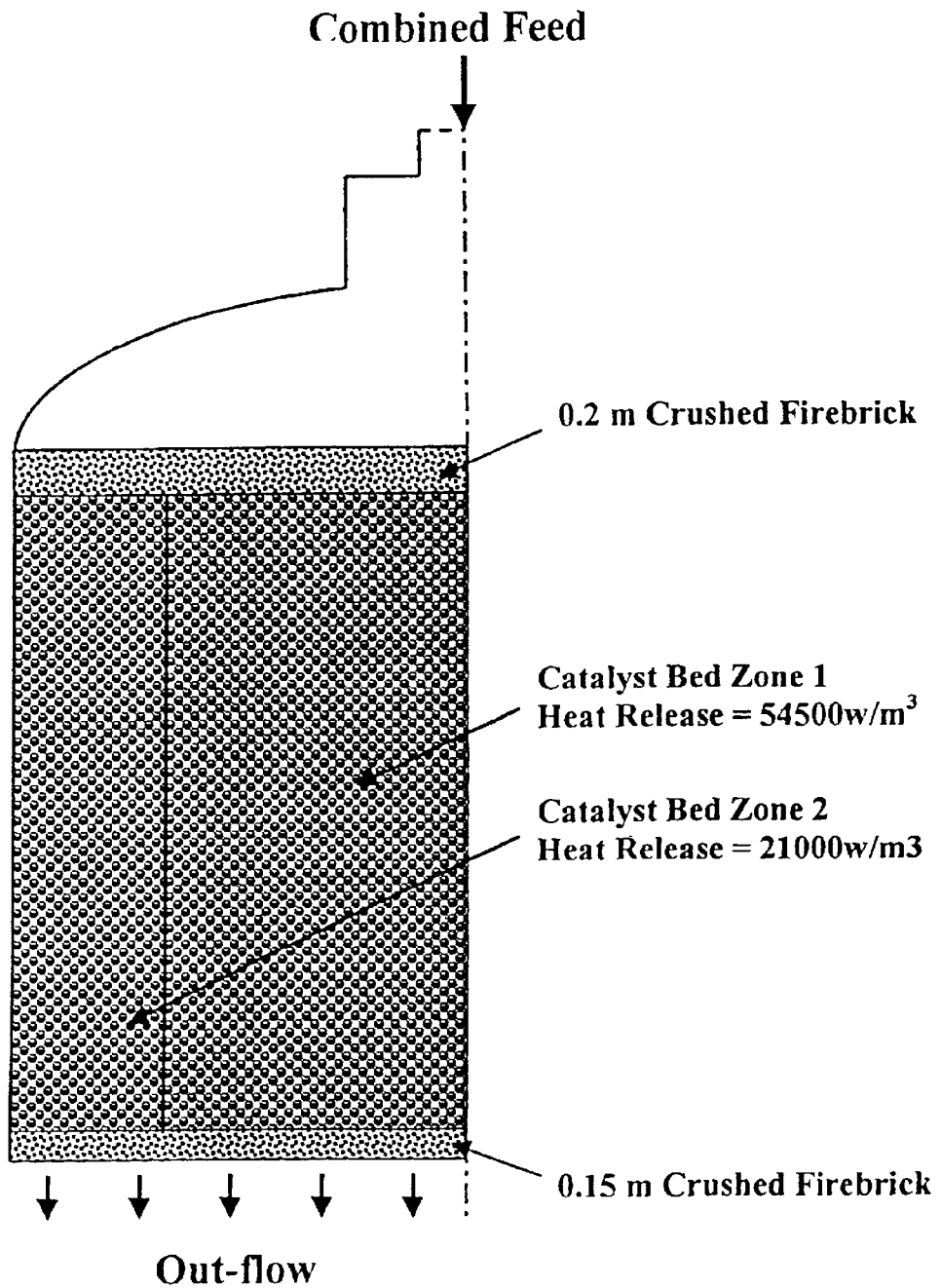
FIG. 2 is a schematic cross-section of half of a catalyst bed in a downflow reactor upon which flow modeling was based assuming constant axial heat release.

FIG. 2 shows the half-section of a downflow reactor upon which the modeling was based. To promote a disparity along the radial displacement in the reactor catalyst bed, a catalyst bed zone 1 was assumed to have a heat release of 54,500 watts per cubic meter whereas an outer radial catalyst bed zone 2 was assumed to have a heat release of 21,000 watts per cubic meter closer to the outside of the reactor. The radius of the boundary between the zone 1 and the zone 2 was set at 1.02 meters to equalize the respective volumes of the zones. The same conditions were also assumed for modeling with respect to an upward flow reactor as shown in FIG. 3.

Figure 3:
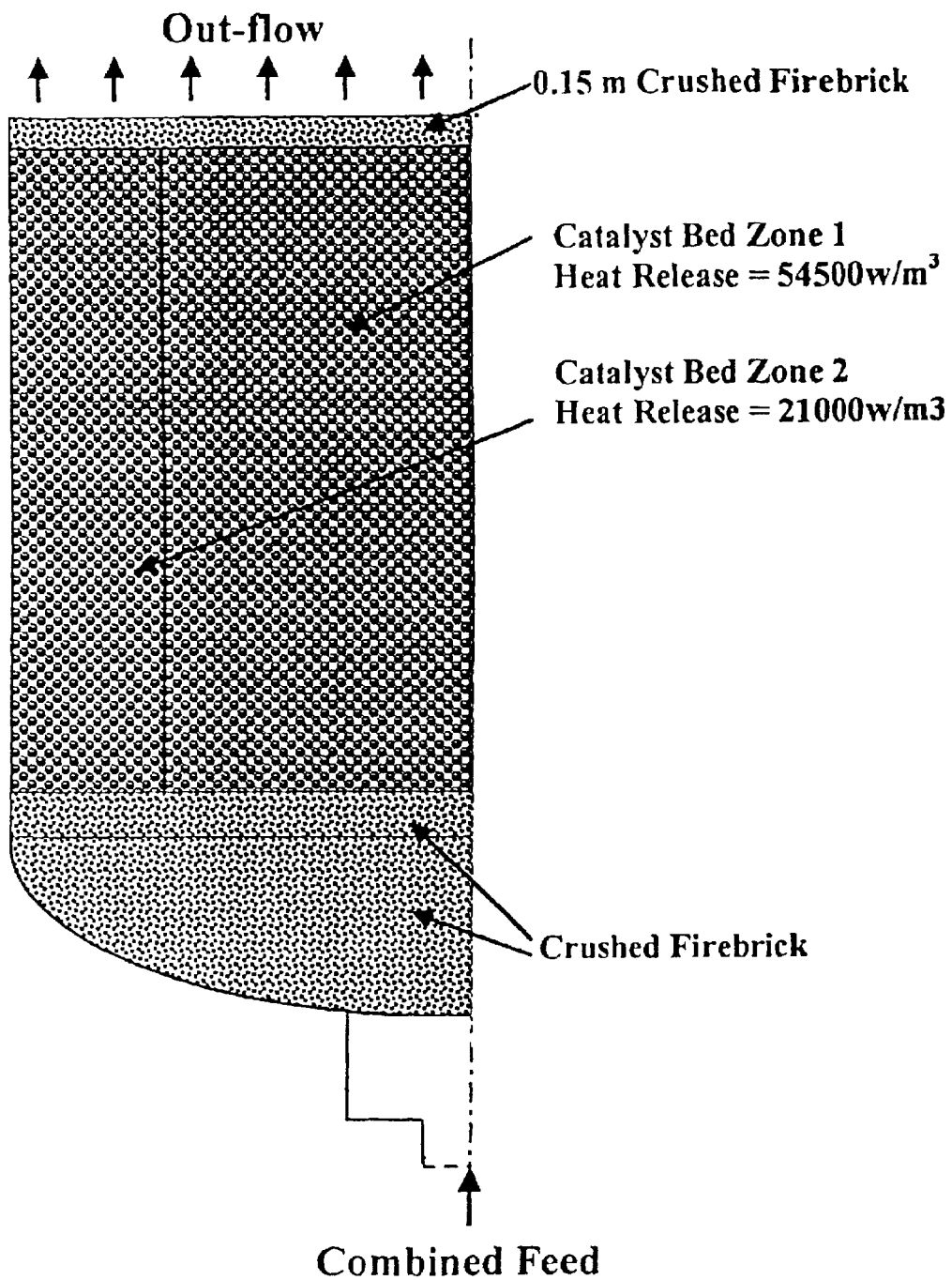
FIG. 3 is a schematic cross-section of half of a catalyst bed in an upflow reactor upon which flow modeling was based assuming constant axial heat release.
Figure 4:
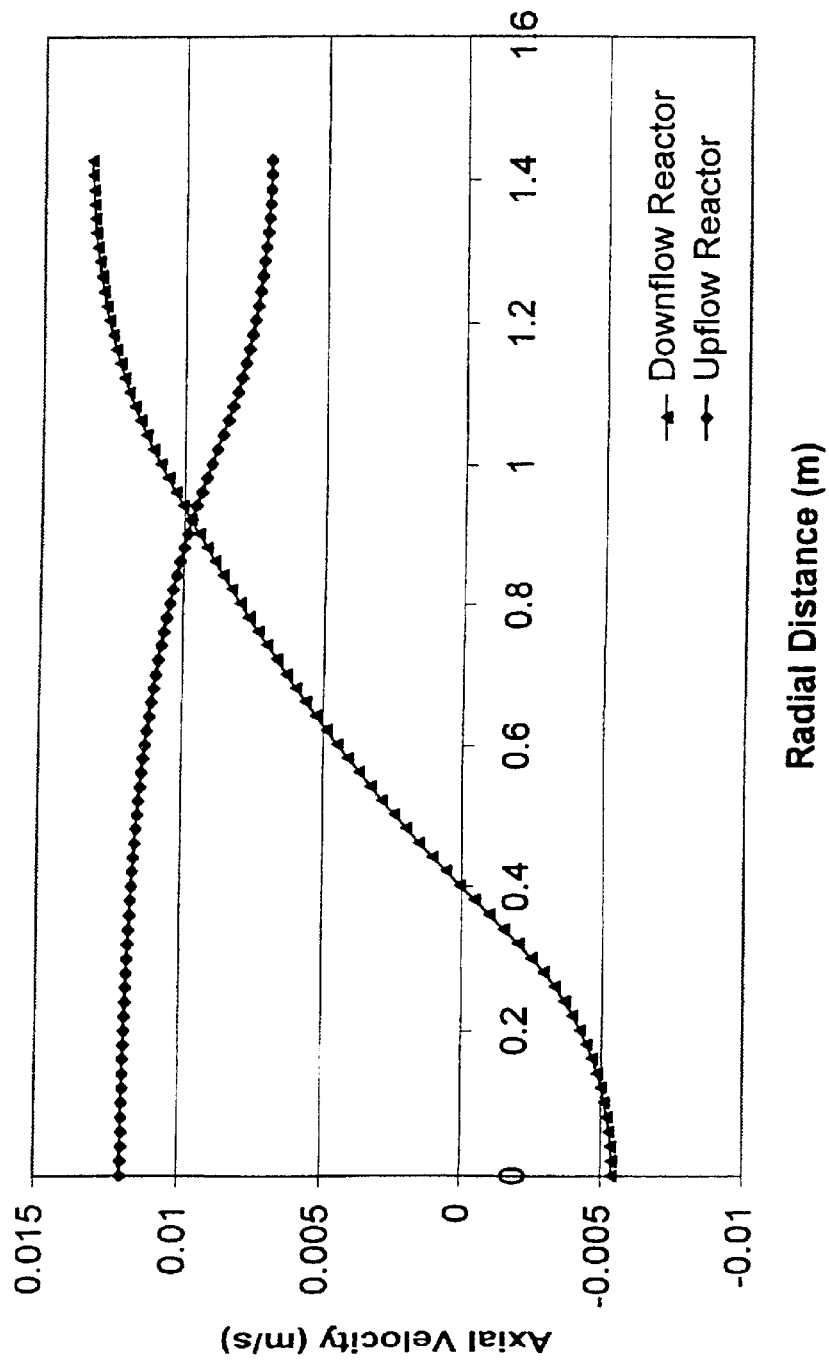
FIG. 4 is an axial velocity radial profile comparing the models represented in FIGS. 2 and 3.

FIG. 4 is a plot of the axial velocity radial profile at 0.3 meters from the outlet of the catalyst bed comparing the upflow reactor scheme in FIG. 3 to the downflow reactor scheme in FIG. 2. In the plot of axial velocity as a function of radial distance from the center of the reactor, the axial velocity slows to 0 at 0.4 meters and begins to have a negative axial velocity near the center of the reactor. This indicates that not only is there bypassing of liquid along the front of the reaction, thereby destroying plug flow reaction conditions, but that some of the reactants are actually recirculating, i.e., flowing upwardly in a downflow reactor. Consequently, much of the feed stream reactants will spend a longer residence time in the reactor in contact with the catalyst which can cause over-oligomerization, thereby generating olefins with higher carbon numbers than desired. Moreover, the excessive residence times can generate more heat from reactions and cause coke to deposit on the catalyst, thereby degrading catalyst performance. On the other hand, the upflow reactor exhibits a fairly steady axial velocity, right around 0.01 meters per second, along the radial profile. The axial velocity dips below 0.01 meter per second at about 0.9 meters which may account for the smaller heat release in the zone 2 which boundary is set at 1.02 meters. However, the disparate heat release between the zones 1 and 2 in the upflow reactor only manifests a slight change in axial velocity, thereby maintaining close to plug flow conditions. The advantage of the upflow reactor versus the downflow reactor in liquid phase conditions was surprisingly significant.

Figure 5:
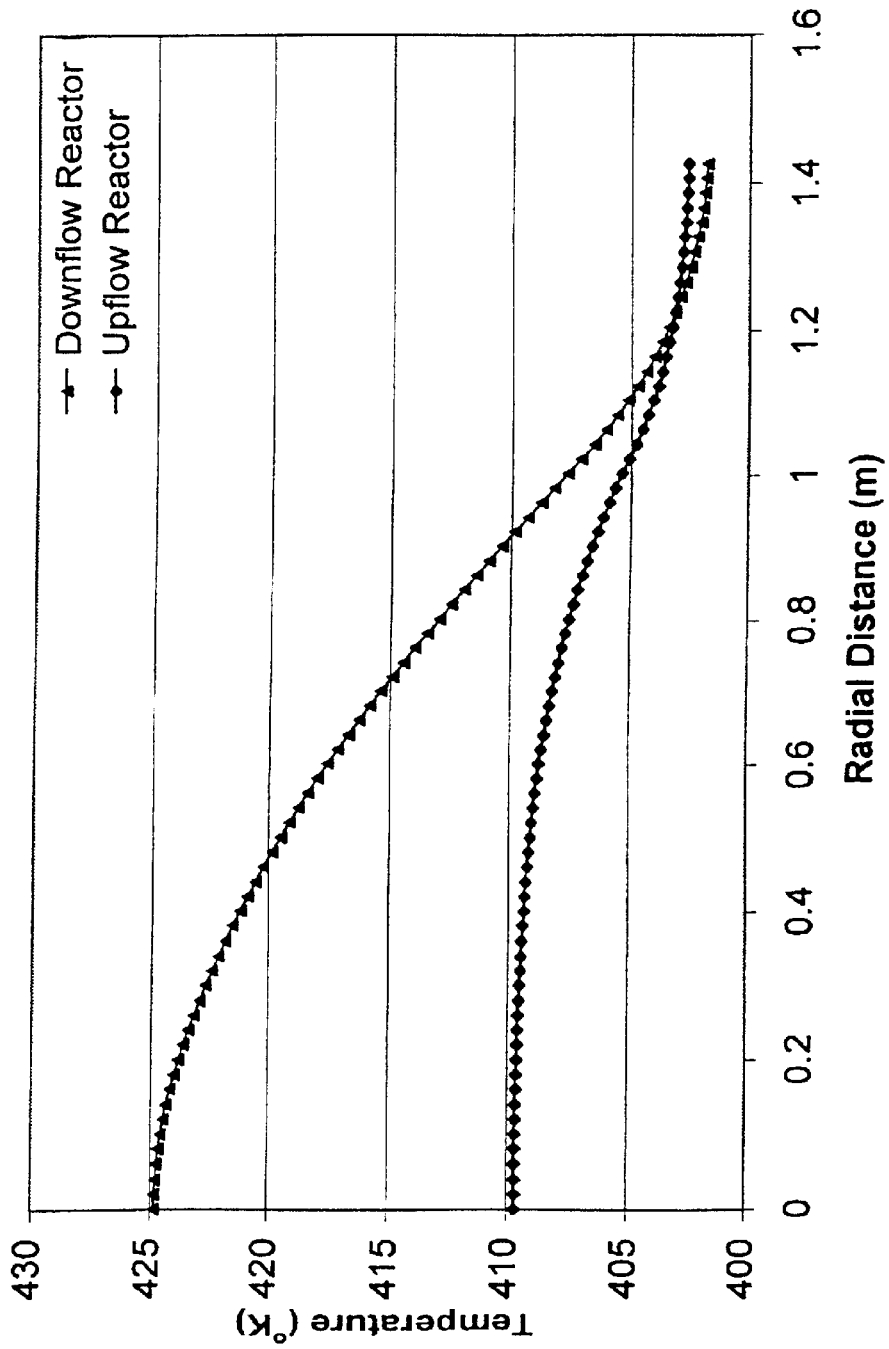
FIG. 5 is a temperature radial profile for constant heat release comparing the models represented in FIGS. 2 and 3.

FIG. 5 shows a comparison of the temperature radial profile for the upflow reactor versus the downflow reactor. The downflow reactor exhibits over about a 23° C. temperature variation between the center and the wall of the reactor. Whereas, the temperature radial profile for the upflow reactor does not vary more than about 7.5° C. The extent of the improvement in the temperature stability of the upflow reactor versus the downflow reactor was also surprising.

EXAMPLE 2

Figure 6:
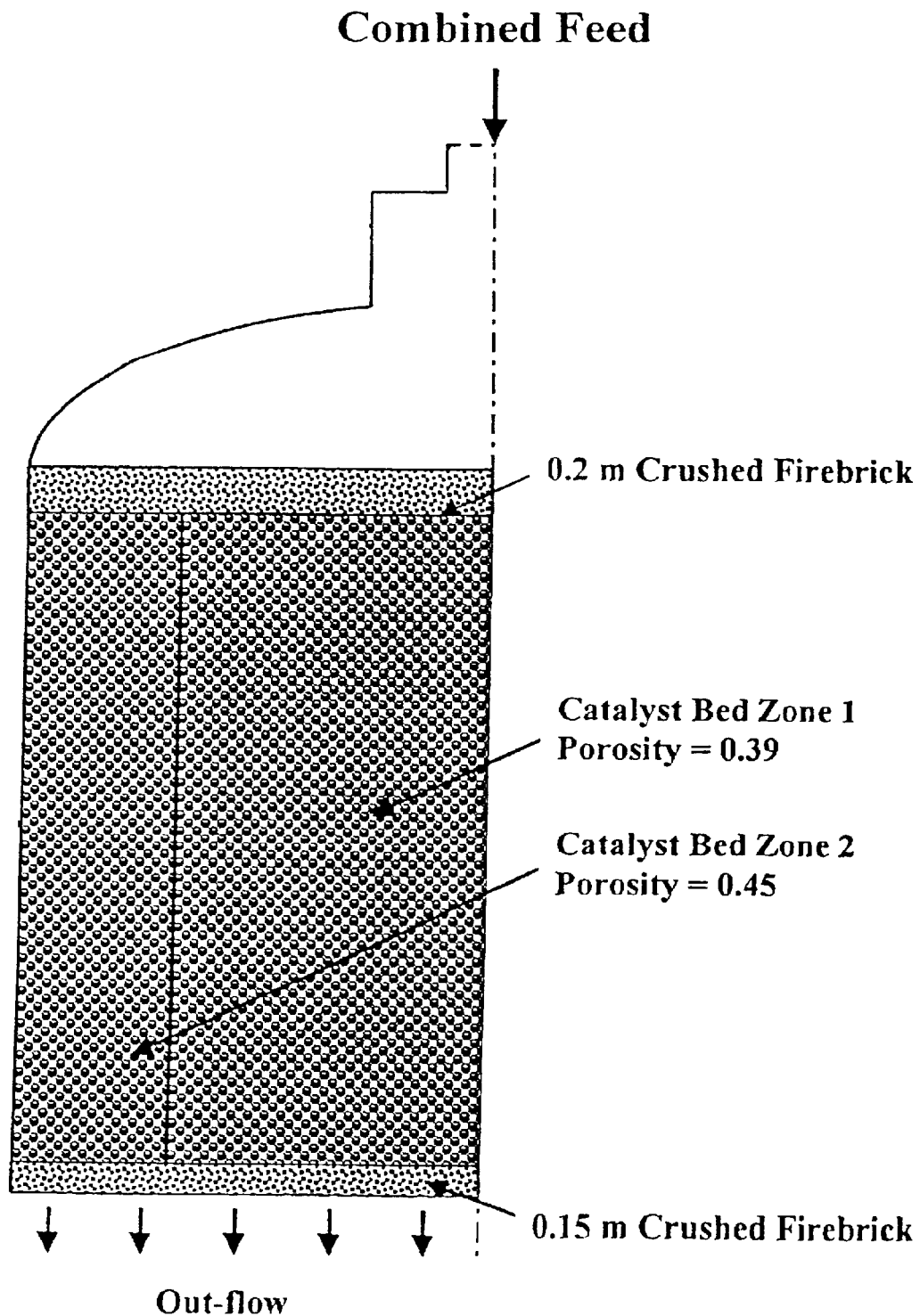
FIG. 6 is a schematic cross-section of half of a catalyst bed in a downflow reactor upon which flow modeling was based accounting for reaction kinetics.
Figure 7:
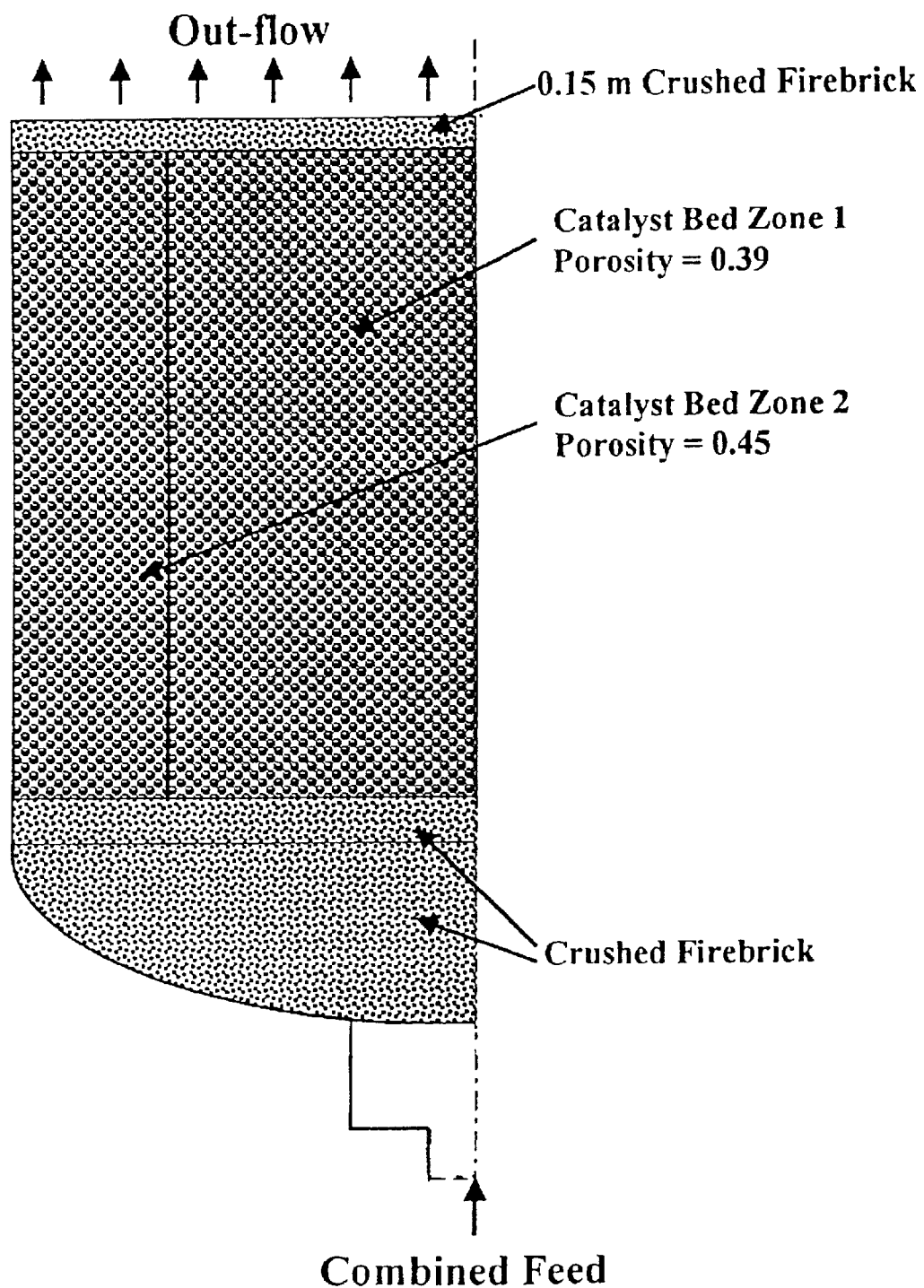
FIG. 7 is a schematic cross-section of half of a catalyst bed in an upflow reactor upon which flow modeling was based accounting for reaction kinetics.

An additional study was conducted using Computational Fluid Dynamics modeling in which reaction kinetics, density, viscosity and heat capacity of the liquid mixture were made functions of both temperature and composition. The model for the downflow reactor is illustrated in FIG. 6, whereas the model for the upflow reactor is shown in FIG. 7. The upflow reactor was assumed to have a diameter of 2.9 meters and a catalyst bed height of 2.5 meters.

It was assumed that only butylene would be in the feed stream as a reactant with the remainder being paraffin diluent. Inlet conditions included mass fractions of isobutylene at 0.1191, of normal butylene at 0.1889 and paraffin diluent, comprising mostly octanes, at 0.6920. Moreover, the inlet temperature was assumed to be 103° C. and the inlet velocity was assumed to be 1.03 meters per second. The inlet viscosity was calculated to be $1.44 \times 10^{-4}$ kg/m/s and the inlet density was calculated to be 567 kg/m$^3$. To approximate the reaction kinetics, it was assumed that three reactions would occur in the oligomerization:

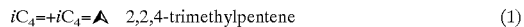

(1)

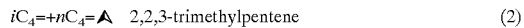

(2)

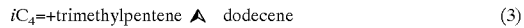

(3)

It was also assumed that isobutylene would undergo a conversion of 97% whereas normal butylene would undergo a conversion of 25%. Moreover, it was assumed that 5% of the reaction heat would be lost through the wall of the reactor. To simulate a disparity in the reactor, the zone 1 of the catalyst bed was given a porosity of 0.39 whereas the zone 2 of the catalyst bed was given a porosity of 0.45. As with Example 1, the boundary between the zone 1 and the zone 2 was set at 1.02 meters.

Figure 8:
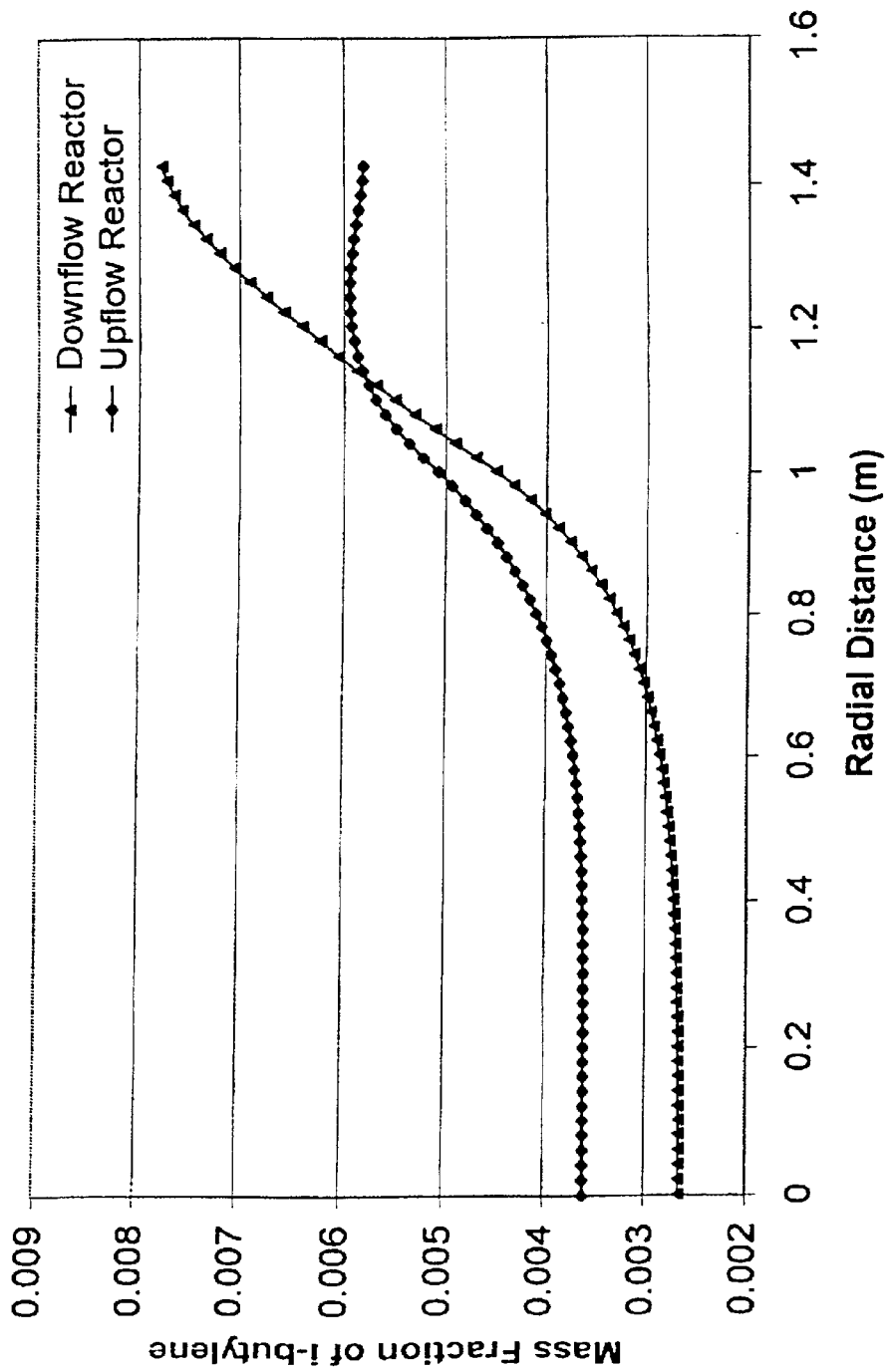
FIG. 8 is a plot of isobutylene radial distribution comparing the models represented in FIGS. 6 and 7.

Results of the model are displayed in FIG. 8 which plots the mass fraction of isobutylene reactant as a function of radial distance from the center of the reactor. The mass fraction distribution of reactant will have a direct impact on the quality of the product distribution. These mass fraction distributions were determined at an axial location of 0.3 meters from the outlet of the catalyst bed. FIG. 8 shows that the radial distribution of mass fraction of isobutylene for the downflow reactor varies widely from about 0.0026 at center to 0.0077 at the wall of the reactor. Whereas, the radial distribution of the mass fraction of isobutylene for the upflow reactor has a tighter distribution from about 0.0036 at the center of the reactor to about 0.0059 at about 1.2 meters from the center of the reactor. The disparate porosity between the zone 1 and the zone 2 affects the butylene distribution in both flow schemes, but the disturbance in the radial distribution of mass fraction of isobutylene only varies about 64% in the upflow reactor. Whereas, the disturbance in the radial distribution of isobutylene in the downflow reactor is over 196%. Hence, the upflow reactor can handle significant disturbances without substantially destroying plug flow conditions and thereby avoiding substantial degradation of product quality. Under the same disparity, the downflow reactor deviates substantially from plug flow conditions, thereby causing substantial product degradation. The extent of improvement in product distribution of upflow reactor over downflow reactor processes indicated by this model was surprising. Similarly, FIG. 9 shows the radial distribution of the mass fraction of normal butylene as a function of radial distance from the center of the reactor. The downflow reactor exhibited a much wider distribution from 0.1398 at the center of the reactor to about 0.1451 at the wall of the reactor whereas the upflow reactor again exhibited a tighter distribution at about 0.1408 at the center of the reactor to about 0.1435 at the wall of the reactor. This wider distribution for the downflow reactor as compared to the upflow reactor demonstrates that plug flow conditions and, therefore product quality, are much more easily maintained in the upflow reactor when a dramatic porosity disparity is simulated.

We expect the same surprising results in Examples 1 and 2 to occur with a resin catalyzed oligomerization system because the reactants, products and heats of reaction will be the same for both resin catalyzed and SPA catalyzed oligomerization systems.

What is claimed is:

1. An oligomerization process for the production of higher aliphatic olefins, said process comprising:

a) passing a liquid oligomerization feed stream comprising lighter aliphatic olefins to a reactor vessel;

b) transporting said liquid oligomerization feed stream upwardly in said reactor vessel against gravity through a fixed bed of resin oligomerization catalyst under oligomerization conditions, said catalyst having a Hammett acidity value of −4 or less;

c) passing a stream of modifier into contact with said feed stream and said catalyst; and d) recovering a liquid oligomerization effluent stream comprising product higher aliphatic olefins.

2. The process of claim 1 wherein the oligomerization conditions include a temperature of 40° to 150° C. (104° to 302° F.), a pressure of 1380 to 2413 kPa (200 to 350 psig) and a liquid hourly space velocity of 1 to 6 $hr^{-1}$.

3. The process of claim 1 wherein said oligomerization conditions include a temperature in a range of from 40° to 150° C. (104° to 302° F.).

4. The process of claim 1 wherein said oligomerization effluent stream is passed to a separator and separated into a product stream comprising said higher aliphatic olefins and lighter olefins.

5. The process of claim 1 wherein said stream of modifier comprises alcohol.

6. The process of claim 1 wherein said oligomerization occurs predominantly in the liquid phase.

7. The process of claim 1 wherein the density of the higher aliphatic olefins in the reactor is less than the density of the lighter aliphatic olefins in the reactor.

8. The process of claim 1 wherein the reactor vessel includes more than one fixed catalyst bed.

9. The process of claim 1 wherein the lighter aliphatic olefins include butenes.

10. The process of claim 1 wherein the higher olefins have a carbon number of at least 6.

11. The process of claim 1 wherein said higher aliphatic olefins include octenes.

12. The process of claim 1 wherein an inert material is disposed in the reactor vessel between the fixed bed of catalyst and a reactor vessel feed inlet.

13. The process of claim 1 wherein said higher aliphatic olefins comprise dimerized or trimerized lighter aliphatic olefins.

14. The process of claim 1 wherein modifier is recovered from the oligomerization effluent and recycled to said reactor vessel.

15. An oligomerization process for the production of $C_6$ or higher aliphatic olefins, said process comprising a) passing a liquid oligomerization feed comprising $C_3$ or higher aliphatic olefins to a reactor vessel;

b) transporting said liquid oligomerization feed upwardly in said reactor vessel against gravity through a fixed bed of acidic catalyst under oligomerization conditions;

c) passing a liquid stream comprising compounds with at least three carbons into contact with said feed stream and said catalyst; and d) recovering a liquid oligomerization effluent stream comprising $C_6$ or higher aliphatic olefin product.

16. The process of claim 15 wherein said oligomerization occurs in the liquid phase.

17. The process of claim 15 wherein the density of the effluent stream in the reactor vessel is less than the density of the feed stream in the reactor vessel.

18. The process of claim 15 wherein the reactor vessel includes more than one fixed catalyst bed.

19. A process for the oligomerization of lighter aliphatic olefins to higher aliphatic olefins comprising a) passing a liquid oligomerization feed stream comprising lighter aliphatic olefins to a reactor vessel, said oligomerization feed stream having a first density;

b) transporting said liquid oligomerization feed stream upwardly in said reactor vessel against gravity through a fixed bed of solid oligomerization catalyst wider oligomerization conditions, said catalyst having a Hammett acidity value of −4 or less; and c) recovering a liquid oligomerization effluent stream comprising product higher aliphatic olefins, said oligomerization effluent stream having a second density that is less than said first density of said oligomerization feed stream.

* * * * *